(12) United States Patent
Trainoff

(10) Patent No.: US 7,386,427 B2
(45) Date of Patent: Jun. 10, 2008

(54) METHOD FOR CORRECTING THE EFFECTS OF INTERDETECTOR BAND BROADENING

(75) Inventor: Steven P. Trainoff, Goleta, CA (US)

(73) Assignee: Wyatt Technology Corporation, Santa Barbara, CA (US)

(*) Notice: Subject to any disclaimer, the term of this patent is extended or adjusted under 35 U.S.C. 154(b) by 534 days.

(21) Appl. No.: 10/665,903

(22) Filed: Sep. 18, 2003

(65) Prior Publication Data

US 2005/0075851 A1    Apr. 7, 2005

(51) Int. Cl.
*G06F 17/10* (2006.01)
*B01D 15/08* (2006.01)

(52) U.S. Cl. .................. 703/2; 210/656; 210/198.2
(58) Field of Classification Search ............. 703/2; 210/656, 198.2
See application file for complete search history.

(56) References Cited

U.S. PATENT DOCUMENTS 5,528,366 A * 6/1996 Shortt .................. 356/344
5,676,830 A * 10/1997 Janik et al. ............. 210/198.2
6,651,009 B1 * 11/2003 Trainoff et al. ........... 702/23

FOREIGN PATENT DOCUMENTS

EP        0 665 433 A1    8/1995

OTHER PUBLICATIONS

C. Jackson, H. G. Barth, "Molecular Weight Sensitive Detectors for Size Exclusion Chromatography," Chapter 4, Handbook of Size Exclusion Chromatography and Related Techniques (2nd Edition), Ed. Chi-san Wu, 2004, pp. 99-138, Marcel Dekker, New York.

C. Jackson and W.W. Yau, "Computer simulation study of size-exclusion chromatography with simultaneous viscometry and light scattering measurements," Journal of Chromatography, 1993, pp. 209-217, vol. 645, Elsevier Science, Amsterdam.

David W. Shortt, "Measurement of narrow-distribution polydispersity using multi-angle light scattering," Journal of Chromatography A, 1994, pp. 11-20, vol. 686, Elsevier.

W.W. Yau, et.al., "Improved computer algorithm for characterizing skewed chromatographic band broadening: II. Results and comparisons," Journal of Chromatography, 1993, pp. 69-77, vol. 630, Elsevier Science, Amsterdam.

* cited by examiner

*Primary Examiner*—Paul Rodriguez
*Assistant Examiner*—Juan Carlos Ochoa
(74) *Attorney, Agent, or Firm*—Philip J. Wyatt

(57) ABSTRACT

Chromatographic separations are often characterized by multiple detectors through which the sample flows serially. As the sample flows between detectors, it becomes progressively diluted due to mixing and diffusion. This phenomenon is traditionally called interdetector "band broadening" and often results in significant distortion of the sample's derived physical properties such as molar mass. A method to characterize the broadening present in a chromatographic system, and an algorithm whereby the narrow peaks of the upstream detector are numerically broadened so they can be compared to the broadened peaks of the downstream detector, is described. Although the technique results in some loss of resolution, its stability and generality allow it a broad range of application. Examples are presented for data collected by dRI, MALS, UV, and viscometric detectors.

12 Claims, 8 Drawing Sheets

US 7,386,427 B2

METHOD FOR CORRECTING THE EFFECTS OF INTERDETECTOR BAND BROADENING

RELATED PATENTS

The methods disclosed in this specification will have particular relevance to a variety of patents and applications by the assignee and inventor. They include the following:

Steven P. Trainoff and Philip J. Wyatt, U.S. Pat. No. 6,651,009, Issued 18 Nov. 2003, Method for determining average solution properties of macromolecules by the injection method.

Philip J. Wyatt, U.S. Pat. No. 6,411,383 25, issued 25 Jun. 2002, "Method for measuring the $2^{nd}$ virial coefficient."

Steven P. Trainoff, U.S. Pat. No. 6,180,906, issued 30 Jan. 2001, "Electrode design for electrical field flow fractionation."

Steven P. Trainoff, et al., U.S. Pat. No. 6,128,080, issued 3 Oct. 2000, "Extended range interferometric refractometer."

Gary R Janik, et al., U.S. Pat. No. 5,900,152, issued 4 May 1999, "Apparatus to reduce inhomogeneities in optical flow cells."

Gary R Janik, et al., U.S. Pat. No. 5.676,830, issued 14 Oct. 1997, "Method and apparatus for reducing band broadening in chromatographic detectors."

Philip J. Wyatt, et al., U.S. Pat. No. 5,530,540, issued 25 Jun. 1996, "Light scattering measurement cell for very small volumes."

David W. Shortt, U.S. Pat. No. 5,528,366, issued 18 Jun. 1996, "Precision determination for molecular weights."

Philip J. Wyatt, U.S. Pat. No. 5,305,071, issued 19 Apr. 1994, "Differential refractometer."

BACKGROUND

The analysis of macromolecular species in solution by liquid chromatographic techniques is usually achieved by preparing a sample in an appropriate solvent and then injecting an aliquot thereof into a chromatograph. The chromatograph includes fractionation devices of various types that separate the sample as it passes through them. Once separated by such means, generally based on size, mass, or column affinity, the samples are subjected to analysis by means of light scattering, refractive index, UV, viscometric response, etc. For example, in order to determine the mass and size distributions of a particular sample whose separation is performed by size exclusion columns, the chromatograph would measure the sample sequentially by multiangle light scattering, MALS followed by a differential refractometer, dRI. The dRI determines the concentration while the MALS unit measures the excess Rayleigh ratio as a function of angle of each eluting fraction. For molecules very much smaller than the wavelength of the incident light, light scattering measurements at a single angle may often be sufficient.

As each fraction passes through a detection device, it produces a signal often referred to as a "band" or "peak." Because of dispersion and mixing effects, these bands are broadened somewhat each time the sample passes through a different device. Consider a sample comprised of a low concentration aliquot of a monodisperse protein. In this event, the Rayleigh excess ratio is directly proportional to the molar mass and the concentration. The light scattering signal and the concentration signal should be of identical shape and would overlay perfectly were the two responses normalized to have the same areas. However, as the sample passes from the MALS detector and enters the dRI detector, it passes through intermediate regions and connections that contribute to the dispersion and mixing of the sample. Many sources of band broadening and some of their remedies are discussed in detail by Yau, et al. in their book "Modem size exclusion liquid chromatography" published by John Wiley & Sons in 1979. In the above example, the dRI signal will always appear somewhat broadened with respect to the MALS signals.

The effect of broadening is shown clearly in FIG. 1 which shows a chromatogram of a sample of bovine serum albumen, BSA, in an aqueous buffer along with the computed molar mass, uncorrected for the effects of broadening. The uncorrected molar mass is shown in trace 1. It is presented divided by the molar mass of the monomer, $M_{w0}$, so that the vertical axis for the monomer reads 1, the dimer reads 2, etc. Trace 2 corresponds to the 90° light scattering signal as a function of time. Trace 3 corresponds to the dRI signal. The aggregation states have been fractionated so that the rightmost peak region, from 16 minutes to 18 minutes, is data from the pure monomer, from 14 minutes to 16 minutes is from the dimer, etc. In each peak, broadening causes the concentration at the center of the peak to be suppressed and that in the "wings" to be enhanced. Combining this broadened dRI signal with the MALS signals to determine molar mass at each elution time causes the molar mass determined near the peak's center to be systematically overestimated, while that in the wings to be underestimated. The situation reverses when the concentration detector is upstream of the MALS detector. This gives rise to the non-constant molar mass data within each peak region. If there were no band broadening, the data would consist of a series of plateaus at 1 for the monomer, 2 for the dimer, etc. As the fractionated sample becomes more polydisperse, the effects of band broadening become less apparent (but are still present). For a well fractionated sample comprised of discrete aggregate states, the problem is obvious. In FIG. 1, the monomer peak is well resolved so the broadening problem is clearest. The aggregates are progressively less well resolved so they show the problem to a lesser extent.

In order to compensate for these distortions, a variety of methods have been employed. Most are based upon the work of L. H. Tung presented in his 1969 paper published in the Journal of Applied Polymer Science, volume 13, p 775 et seq. The afore-referenced book by Yau et al. discusses some of the means to correct band broadening. Throughout the chromatography literature, many papers address means to perform these corrections, i.e. to restore the broadened band to the shape it would have had were no broadening sources present. Most of the techniques are numerically unstable and can result in physically unreasonable results, such as negative concentrations, or negative scattered intensities, and therefore are rarely used. The characterization of proteins by MALS measurements represents an area of particular importance, yet even here, band-broadening corrections are rarely seen because of the difficulties associated with their implementation.

Band broadening effects occur in a variety of multi-detector implementations of liquid chromatography. For example, if a sample is to be measured by an on-line viscometer so that its intrinsic viscosity may be determined, then a dRI will also be needed. As the sample passes from the dRI to the viscometer, it will experience band broadening resulting in a spreading of the specific viscosity curve with respect to the concentration curve derived from the dRI measurement. Again, the computational difficulties, associated with restoring the broadened signal to conform to what it would have been without broadening, often result in questionable results, especially if the samples are indeed monodisperse such as unaggregated proteins.

It is the purpose of the present invention to provide an analytical method by which band-broadening effects may be corrected in software with both ease and precision. Another objective of the invention is to provide a new approach to such corrections whose departure from the conventional approach is sharply distinguished therefrom. The present invention is expected to be of greatest utility for the analysis of separations of protein samples. A consequence of this application will be the more precise characterization of protein conjugates as well as aggregate states. A further application of this invention is its ability to improve the determination of intrinsic viscosity measurements by correcting the band broadening effects associated with the sample passage between a concentration detector and a viscometer. An important application of the invention will be its application to the rapid determination of the $2^{nd}$ virial coefficient of an unfractionated sample as discussed, for example, in U.S. Pat. No. 6,411,383 and the application Ser. No. 10/205,637 filed 24 Jul. 2002, now in process of issuance, by Trainoff and Wyatt. The successful implementation of that method depends critically upon the ability to determine accurately the square of the concentration at each elution volume. This requires an accurate measurement of the concentration at each such elution volume. The latter determinations are made generally on unfractionated samples whose detector responses are a single peak whose mass composition is the same at each interval collected. This single peak is broadened as it proceeds through the series of detectors leading to systematic errors in the derived results, unless the effect of broadening is corrected.

SUMMARY OF THE INVENTION

Figure 1:
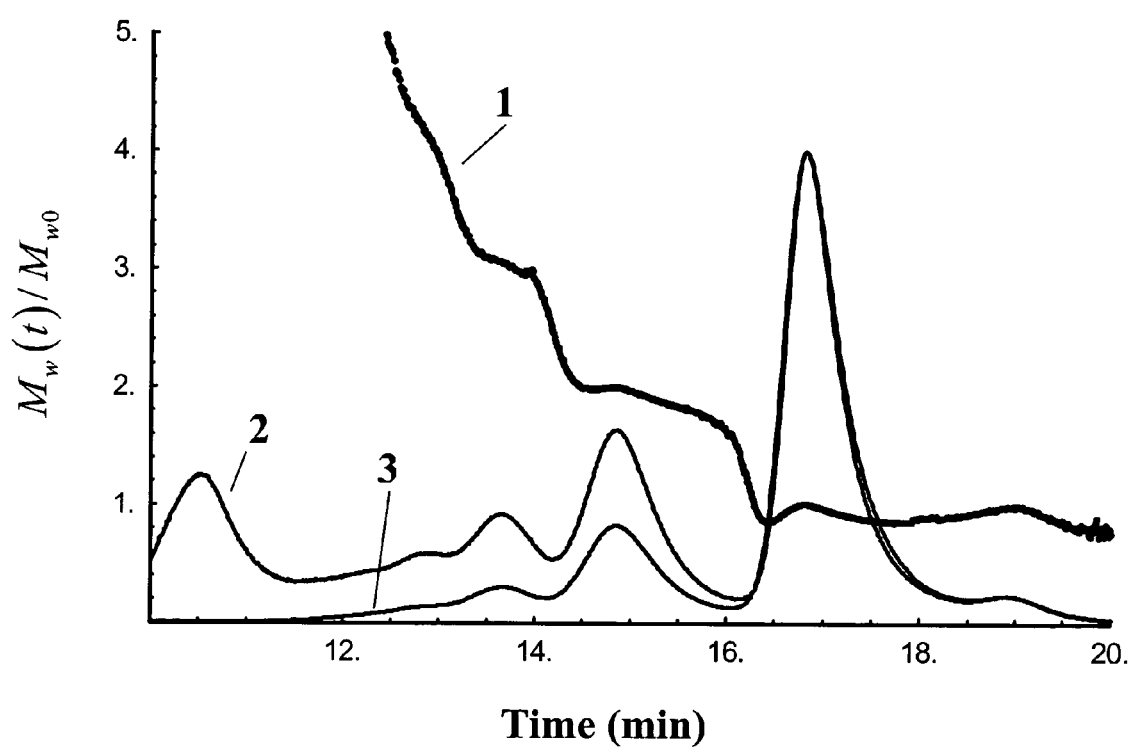
FIG. 1 shows an uncorrected plot of the molar mass of a BSA sample with the dRI detector downstream of MALS detector.

The present invention comprises a method to correct for band broadening effects occurring between detectors of a liquid chromatograph. Rather than correct the band broadening produced at a second detector by restoring the band to the form of the first, the method broadens the band of the first detector to conform to the broadened band at the second. This results in a simpler, more robust, and more easily implemented means to correct band-broadening effects at all detectors. Although the method can result in reduced peak resolution when peaks overlap partially, areas of major application are expected to be for monodisperse samples with well-separated and resolved peaks. The invention is applicable as well to any number of serially connected detectors.

DETAILED DESCRIPTION OF THE INVENTION

Molecules in solution are generally characterized by their weight averaged molar mass $M_w$, their mean square radius $<r_g^2>$, and the second virial coefficient $A_2$. The latter is a measure of the interaction between the molecules and the solvent. For unfractionated solutions, these properties may be determined by measuring the manner by which they scatter light using the method described by Bruno Zimm in his seminal 1948 paper that appeared in the Journal of Chemical Physics, volume 16, pages 1093 through 1099. More recently, the method discussed in U.S. Pat. No. 6,651,009 by Trainoff and Wyatt, represents an advanced technique that will replace the more traditional Zimm approach.

The light scattered from a small volume of the solution is measured over a range of angles and concentrations. The properties derived from the light scattering measurements are related through the formula developed by Zimm:

$$R(\theta)=K^*M_w cP(\theta)[1-2A_2 M_w cP(\theta)]+O(c^3), \quad (1)$$

where $R(\theta)$ is the measured excess Rayleigh ratio in the direction $\theta$ per unit solid angle defined as $R(\theta)=[I_s(\theta)-I_{solv}(\theta)]r^2/I_0 V$, $I_s(\theta)$ is the intensity of light scattered by the solution per unit solid angle, $I_{solv}(\theta)$ is the intensity of light scattered from the solvent per unit solid angle, $I_0$ is the incident intensity, r is the distance from the scattering volume to the detector, V is the illuminated volume seen by the detectors, $P(\theta)$ is the form factor of the scattering molecules defined as $$P(\theta) = \lim_{c \to 0} R(\theta)/R(0),$$

$K^*=4\pi^2(dn/dc)^2 n_0^2/(N_a\lambda_0^4)$, $N_a$ is Avogadro's number, $dn/dc$ is the refractive index increment, $n_0$ is the solvent refractive index, c is the concentration, and $\lambda_0$ is the wavelength of the incident light in vacuum. The incident collimated light beam is assumed vertically polarized with respect to the plane containing the light scattering detectors. The form factor is related to the mean square radius $<r_g^2>$ by $$P(\theta) = 1 - \frac{16\pi^2 n_0^2}{3\lambda_0^2}\langle r_g^2\rangle \sin^2(\theta/2) + O(\sin^4(\theta/2)) \quad (2)$$

Multiangle light scattering instruments measure the amount of light scattered from a fluid sample as a function of both angle and time. For molecules very small compared to the wavelength of the incident light, light scattering measurements may be restricted to a single scattering angle, such as 90°, since there would be no measurable variation of the scattered intensity with angle, however in this limit, the molar mass may be measured, but the mean square radius may not.

When the instrument is used to analyze the eluant of a separation system, such as size exclusion chromatography, SEC, the sample composition and concentration change with time. Furthermore, SEC columns typically dilute the sample concentration so that the second and third terms on the right hand side of Eq. (1) can be neglected compared to the first. Formally this is the case when $$2A_2 cM_w \ll 1. \quad (3)$$

Typically, for chromatographic separations combined with light scattering instrumentation, the above condition is assumed unless A2 is known from prior experiment, in which case such value may be used in Eq. 1 directly. In addition, if the separation is performed properly, at each point in time the sample is essentially monodisperse in size, and usually in mass. If the sample is also monodisperse in mass we have the further simplification that $$R(\theta,t)=K^* Mc(t) P(\theta,t). \quad (4)$$

Therefore, the light scattering signal should be directly proportional to the concentration signal and the molar mass can be computed by the ratio $$M = \frac{1}{K^* c(t)} \lim_{\theta \to 0} R(\theta, t). \quad (5)$$

A common test for the correct operation of a MALS system is to inject a nearly monodisperse sample through a separation column, and then measure both the light scattering and the concentration signals for a monodisperse peak. If normalized, they should overlay exactly at all elution times corresponding to the constancy expressed by Eq. (5). However, if the concentration detector is downstream of the MALS detector, two effects will change the shape of the peak: mixing and diffusion. When this is the case, the peak appears broadened; the center of the peak is suppressed and the "wings" are enhanced. Therefore, when the ratio in Eq. (5) is formed, it will not be constant and the molar mass derived near the peak will be systematically overestimated, while that near the wings will be underestimated. The situation is reversed when the concentration detector is upstream of the MALS detector.

It should be pointed out that samples injected into a chromatograph without fractionation, often described as flow injection, also experience band broadening during their passage from one detector to another. Although the molar mass distribution at each successive elution volume are expected to remain constant, band broadening effects will affect various weight average properties derived from downstream broadening at selected detectors. Thus an injected sample peak comprised of a polydisperse molar mass distribution will broaden as it passes, for example, between a light scattering detector and a dRI concentration detector. When the unfractionated light scattering signals are combined with the broadened concentration detector signal, the derived weight averaged molar mass near the center of the peak will be calculated to be larger while the corresponding values in the wings will be smaller. This result is exactly equivalent to that seen for fractionated samples.

Sample mixing primarily depends on the geometry of the system: the length and diameter of the tubing, the number of unions, the roughness of the surfaces, and the number of inclusions caused by mechanical defects, and the geometry of the measurement cells. The effect of mixing is primarily independent of the sample composition in the limit that the bulk fluid properties, such as viscosity, are not substantively changed by the sample. Diffusion, in contrast, depends explicitly on the sample properties.

It is instructive to estimate the relative importance of diffusion and mixing for a sample flowing between two detectors. For uniform spheres the Stokes-Einstein relation $$D_T = \frac{k_B T}{6\pi \eta r}, \quad (6)$$

relates the diffusion constant $D_T$ to the sphere radius r, where $k_B$ is Boltzmann's constant, T is the absolute temperature, and $\eta$ is the solvent viscosity.

There are many sources of mixing, but to estimate the scale, consider the simple model of a well-mixed reservoir. Assume that the light scattering flow cell is a mixing chamber with a volume V. Let the flow rate be denoted f, and assume that the concentration of the sample entering the chamber is $c_i(t)$. The concentration of the sample exiting the flow cell is given by $$c'(t)=[c_i(t)-c(t)]/t_f, \quad (7)$$

where $t_f=V/f$ is the time to fill the reservoir. Consider the effect of a narrow pulse, containing a mass $m_0$ of sample injected into the flow cell so that $c_i(t)=m_0\delta(t)$. The concentration of the sample exiting the cell is then $$c(t) = \frac{m_0}{t_f} \exp(-t/t_f)\theta(t), \quad (8)$$

where $\theta(t)=0$ for $t<0$ and $\theta(t)=1$ for $t \geq 0$. To put this in context, assume that the flow cell has a volume of V=80 μl and is fed by a flow rate of f=1.0 ml/min. The exponential time constant for the broadening is $t_f$=4.8 sec. If this mixing chamber is fed and drained by capillary tubing with an internal diameter of 0.25 mm, the initially localized concentration pulse is smeared out over a length of tubing 1.6 m in length. Of course, when the sample flows through the light scattering cell, it is not "well mixed," but this is a good estimate of the length scale of the mixing.

Next, consider the effect of diffusion for a small molecule. The molecules will diffuse, on average, a distance $$\langle |x| \rangle = \sqrt{2 D_T t} \quad (9)$$

where, $D_T$ is the molecule's translational diffusion constant and t is time. Again, to put this in context, consider the protein bovine serum albumen, BSA, which has a diffusion constant of $7.7 \times 10^{-7}$ cm²/sec. How far does the concentration spike diffuse in 4.8 sec ? Equation (9) indicates that it will diffuse along the tubing a mere 27 μm ! Therefore, we conclude that the dominant mixing mechanism is non-diffusive in origin and therefore should not depend on the diffusion constant, and hence the size, of the molecule. The dominate mechanism of inter-detector broadening is due to mixing and is sample-independent. Therefore if the geometrical broadening of the system can be characterized with a reference sample, the resulting broadening parameters can then used to correct all subsequent data runs.

Consider a simple linear model for interdetector broadening. For the purposes of discussion, assume that the concentration detector is located downstream of the MALS detector. Furthermore, assume that Eq. (3) is satisfied, and that data for a monodisperse reference sample has been collected. Therefore, the measured concentration depends on the underlying concentration in the MALS detector via the convolution with a parameterized broadening function $B(\alpha_0, \alpha_1, \ldots, \alpha_l, \tau)$. One has $$c^m(t) = \int_{-\infty}^{\infty} c(t-\tau) B(\alpha_0, \alpha_1, \ldots, \alpha_l, \tau) d\tau, \quad (10)$$

where $c^m(t)$ is the measured concentration at the downstream detector following broadening, and $c(t)$ is the concentration of the sample when it passed through the light scattering detector. The parameters $\alpha_l$ are model specific and include the width of the broadening function and the interdetector delay volume. The goal of the broadening correction is to find the best-fit values of these parameters. According to Eq. (5) one may write $$c^m(t) = \frac{1}{K^*M} \int_{-\infty}^{\infty} R(0, t-\tau) B(\alpha_0, \alpha_1, \ldots, \alpha_l, \tau) d\tau \quad (11)$$

Here we have used the fact that the peak is monodisperse, so that the molar mass M does not change across the peak, and it can be brought outside the integral. In order to determine the best fit parameters, one forms the chi-squared difference between the downstream measured concentration signal, $c^m(t)$, and the broadened upstream light scattering signal and integrates it across the monodisperse sample peak $$\chi(\alpha_0, \ldots, \alpha_l, \tau)^2 = \quad (12)$$

$$\int_{peak} \left( c^m(t) - \frac{1}{K^*M} \int_{-\infty}^{\infty} R(0, t-\tau) B(\alpha_0, \ldots, \alpha_l, \tau) d\tau \right)^2 dt.$$

One may then use a standard nonlinear least squares fitting package to find the best-fit parameters for $K^*M$ and the $\alpha_i$ that minimize $\chi^2$. Denote these best fit parameters $\alpha'_i$.

As a practical matter, one may include other system specific parameters in the above fit. For example, the excess Rayleigh ratio in Eq.(12) is defined as the difference between Rayleigh ratio of the solvent with sample, and the Rayleigh ratio of the pure solvent. The Rayleigh ratio of the pure solvent can be included as an adjustable fit parameter, instead of manually determining it by setting a solvent baseline. Similarly, if the concentration detector has a slow drift, then the offset and slope of the drift can similarly be included in the fit. It is important to note that it is essential that the molar mass is constant over the peak so that the inner integral in Eq.(12)

$$\int_{-\infty}^{\infty} R(0, t-\tau) B(\alpha_0, \ldots, \alpha_n, \tau) d\tau$$

Once the optimal fit parameters have been determined, there are two ways in which they can be used in the subsequent analyses. One can attempt to "narrow" the concentration measurements by performing a deconvolution of Eq. (10) and attempt thereby, to answer the question: what would a concentration detector have measured if it were coincident with the light scattering detector? Alternatively, one can artificially broaden the light scattering results to answer the conceptual question of what would the light scattering results have been if they were performed downstream coincident with the concentration detector? We will argue that the former method, which has formed the traditional approach, is numerically unstable and often gives unphysical results, while the latter method is numerically stable, but at the expense of reducing the resolution of the measurement. Since the broadening is usually a small correction, the loss of resolution is minimal and the latter method is preferable.

Consider the traditional deconvolution method. One may reconstruct $c(t)$ from knowledge of $c^m(t)$ by writing the Fourier Transform $$c(t) = \frac{1}{\sqrt{2\pi}} \int_{-\infty}^{\infty} e^{i\omega t} \frac{\tilde{c}^m(\omega)}{\tilde{B}(\alpha'_1, \ldots, \alpha'_n, \omega)} d\omega, \quad (13)$$

where $$\tilde{c}^m(\omega) = \frac{1}{\sqrt{2\pi}} \int_{-\infty}^{\infty} e^{i\omega t} c^m(t) dt, \quad (14)$$

is the Fourier transform of the measured concentration, and $\tilde{B}(\alpha'_1, \ldots, \alpha'_l, \omega)$ is similarly the Fourier transform of the broadening kernel evaluated with the fit parameters found above. One may then compute the molar mass as a function of time by using Eq. (5). The problem with this procedure lies in computing the ratio $\tilde{c}^m(\omega)/\tilde{B}(\alpha'_1, \ldots, \alpha'_l, \omega)$ Both $\tilde{c}^m(\omega)$ and $\tilde{B}(\alpha'_1, \ldots, \alpha'_l, \omega)$ end towards zero as $\omega \to \pm\infty$. Therefore, the ratio tends towards 0/0 which is indeterminate. Because $\tilde{c}(\omega)$ contains experimental noise, the ratio will have increasing large fluctuations for large $\omega$. Therefore, when one computes $c(t)$ using Eq. (13), the result contains high frequency noise and unphysical "ringing," including negative concentrations. While the noise can be filtered out, the unphysical ringing cannot.

The second method, which is the subject of this patent, is to broaden the light scattering peak. Therefore, we write $$M(t) = \frac{1}{K^*c^m(t)} \lim_{\theta \to 0} \int_{-\infty}^{\infty} R(\theta, t-\tau) B(\alpha'_1, \ldots, \alpha'_l, \tau) d\tau. \quad (15)$$

This constitutes a measurement of the molar mass as a function of time, corrected for interdetector broadening. Note that right hand side of Eq. (15) contains only measurable quantities, along with the broadening function evaluated with the previously determined parameters.

Models of the Broadening Function

The algorithm described above allows one to correct the light scattering results for the effects of interdetector band broadening given a parameterized model of the broadening kernel. However, to apply the algorithm, one must choose a model to use. In this section we will describe a specific model which works well for the MALS hardware, DAWN instruments, built by Wyatt Technology of Santa Barbara, Calif. However, it is important to note that the algorithm applies equally well to any definite model.

The light scattering cell used in the Wyatt MALS instrumentation is a cylinder 1.25 mm in diameter fed, at 90 degrees, by a capillary that is 0.1 mm in diameter, and drained by a capillary that is 0.2 mm in diameter. Typical flow rates are of the order of 1 ml/min. One can determine whether the flow is laminar or turbulent by computing the Reynolds number, defined as Re=$\bar{v}$d/v, where $\bar{v}$ is the average flow velocity, d is a characteristic dimension of the system, and v is the sample viscosity. For the flow in the inlet capillary one has $\bar{v}$=127 mm/sec, d=0.1 mm, and v=0.89 cm$^2$/sec, so that Re=14. Fluid flow typically does not become unstable until it reaches Reynolds number of a few hundred. Therefore, we conclude that the flow in the inlet capillary is laminar. Next, consider the jet of fluid as it enters the flow cell. The flow rate is the same, but the characteristic dimension increases to d=1.25 mm. Therefore, the Reynolds number increases to Re=178. Therefore, we conclude that there is some turbulent mixing near the inlet of the cell, which has a mixing volume of some fraction of the cell volume. Similarly, there is some mixing in the inlet of a concentration detector flow cell.

There is also some instrumental broadening which comes from the fact that the system measures a finite volume of fluid, and the measurement system has some intrinsic filter time constant. Therefore the model we will consider is an exponential broadening, to represent the mixing in the flow cell convolved with a Gaussian term to represent the instrumental broadening. The model for the broadening kernel is $$B(\sigma, w, \tau) = \frac{1}{\sigma\sqrt{2\pi}} e^{-\tau^2/2\sigma^2} \otimes \frac{1}{w} e^{-\tau/w} \theta(\tau), \quad (16)$$

where σ is the instrumental Gaussian width, and w is the broadening due to mixing in the inlet of the cell and the convolution is defined as $$a(t) \otimes b(t) \equiv \int_{-\infty}^{\infty} a(t-t')b(t')dt'. \quad (17)$$

To test the appropriateness of this model, we performed the following test. We filled a 5 μl injection loop with 200 kD polystyrene dissolved in toluene and injected it directly into the light scattering flow cell. The flow rate was 0.5 ml/min and the sample collection interval was 0.25 sec. We model the data as a delta function, to represent the injection loop, convolved with the broadening model. To compare this with the 90° light scattering signal, one forms $\chi^2$ as $$\chi(a, t_0, \sigma, w)^2 = \int_{-\infty}^{\infty} [R(90°, t) - aB(\sigma, w, t-t_0)]^2 dt, \quad (18)$$

where $t_0$ is the time required for the sample to flow from the injector to the flow cell, and a is a scale factor to convert from dimensionless units to Rayleigh ratio. There are four fit parameters: a, $t_0$, σ, and w.

Figure 2:
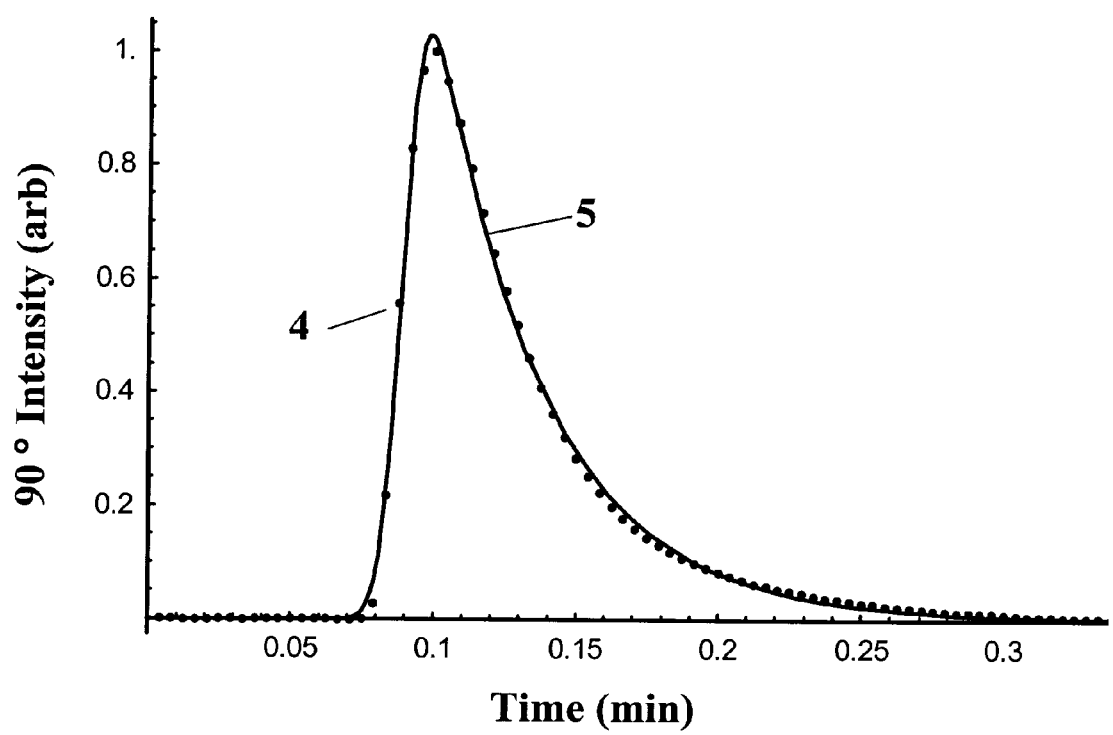
FIG. 2 shows the hybrid broadening model fitted to the 90° light scattering trace of a 5 μl injection of 200 kD polystyrene in toluene.

FIG. 2 shows the results of the fit. The light scattering data points 4 are normalized so the peak has unit amplitude. The resulting fit to the broadening function is 5. This includes only the broadening which occurs between the injection loop and the center of the flow cell, where the measurement takes place. It is clear the broadening function fits the data well, and therefore is an appropriate model for interdetector broadening. This broadening model will be used in demonstrations described below.

Applying the Method to an Arbitrary Series of Detectors

In this section the method will be generalized for two or more arbitrary detectors connected in series. Define the detectors responses as $D_i(t)$, as the sample flows serially from $D_1$, to $D_2$, ... to $D_n$. In general, the sample peaks become progressively broader as they elute through the system. Any analysis on the data $(D_1(t), D_2(t), \ldots, D_n(t))$, will be compromised by this progressive broadening. As before, it is numerically more stable to broaden the upstream detectors to be consistent with the detector with the broadest response. Usually this will be the last detector in the chain. However, if one of the intermediate detectors has a large instrumental broadening, the results can be referenced to it instead. For the purposes of discussion we will assume that the upstream detectors signals will be broadened to match $D_n$.

The procedure has two phases. In the first phase, one determines the broadening parameters by measuring a monodisperse sample at a low enough concentration that the detector signals, in the absence of broadening, would be directly proportional. Practically, one injects a nearly monodisperse sample through the chromatograph, and selects the monomer subpeak with which to determine the broadening parameters. For each detector i from 1 to n−1, one computes $$\chi_i^2(\beta_i, \tau_i, \alpha_{ij}) = \int_{peak} \left(D_n(t) - \beta_i \int_{-\infty}^{\infty} D_i(t-\tau)B(\alpha_{ij}, \tau - \tau_i)d\tau\right)^2 dt, \quad (19)$$

where $\chi_i^2(\beta_i, \tau_i, \alpha_{ij})$, is the chi squared parameter for the i$^{th}$ detector. The parameters $\beta_i$ are proportionality factors which bring the detector signals to the same scale, $\tau_i$ are the inter-detector delays associated with the time it takes the sample to travel from one detector to the next, and $\alpha_{ij}$ are the j broadening parameters for the i$^{th}$ detector. These $\chi^2$ are minimized using a standard nonlinear least squares fit algorithm to determine the best fit parameters, $\beta'_i$, $\tau'_i$ and $\alpha'_{ij}$. Software capable of such fitting is readily available in various commercial packages. The procedures and some of the various software approaches have been discussed in detail by Hiebert in his 1981 paper "An Evaluation of Mathematical Software That Solves Nonlinear Least Squares Problems" in the ACM Transactions on Mathematical Software, volume 7, pages 1-16.

In the second phase, one applies the broadening parameters determined in the first phase to correct all subsequent data runs. In this phase, all of the upstream detector signals are broadened as if they were coincident to the last detector in the chain. Then they can be compared directly to the last detector $D_n$. The broadened data are $$D_i^b(t) = \int_{-\infty}^{\infty} D_i(t-\tau)B(\alpha'_{ij}, \tau - \tau'_i)d\tau, \quad (20)$$

Then the original analysis proceeds on the data sets $(D_1^b(t), \ldots, D_{n-1}^b(t), D_n(t))$.

Demonstration of the Algorithm

In this section we will demonstrate the algorithm on sample data for the following instrument combinations: MALS+dRI, Viscometer+dRI, and UV+MALS. FIG. 1 shows data from an 100 μl injection of BSA into a Shodex OH pack KW protein separation column manufactured by Showa Denko, Japan. The flow rate was 0.5 ml/min. The fractionated sample first passed through the light scattering detector and then the dRI detector. The BSA sample consisted primarily of monomers, but had a substantial content of aggregates which were separated by the column. The peak between 16 min and 18 min primarily consists of pure monomer. The peak between 14.4 min and 16 min is pure dimer, and the subsequent peaks are higher aggregates that are less well separated. The horizontal axis is time in minutes. Trace 1 is the computed molar mass $M_w(t)$ divided by the monomer molar mass $M_{w0}$. Therefore the monomer reads 1 on the vertical axis; the dimer reads 2, etc. Trace 2 is the 90° light scattering signal and trace 3 is the refractive index signal. Both the refractive index and the light scattering have been normalized so that their peaks have the same maximum height. The vertical scale for traces 2 and 3 is arbitrary.

The first step in the algorithm is to choose the broadening model. For the data set in FIG. 1, the hybrid model described in Eq.(16) was used. The second step in the algorithm is to choose a monodisperse peak on which to determine the fit parameters. The monomer peak between 16 mm and 18 mm was used. When one forms the $\chi^2$ in Eq. (19), there are four parameters to be determined by nonlinear least squares fitting. An extra parameter was added to account for a possible baseline shift between the two data sets. Therefore the $\chi^2$ that was minimized was $$\chi^2(\beta, \tau_0, \sigma, w, x_0) = \int_{peak} \left( dRI(t) - \beta \int_{-\infty}^{\infty} LS(t-\tau)B(\sigma, w, \tau-\tau_0)d\tau + x_0 \right)^2 dt, \quad (21)$$

where, LS (t) is the 90° light scattering signal as a function of time, and dRI (t), is the dRI data as a function of time. This model was minimized by using a commercial Marquardt nonlinear least squares package such as described by D. W. Marquardt in his 1963 article in the Journal of the Society of Industrial and Applied Mathematics, "An algorithm for least squares estimation of nonlinear parameters," volume 11, pages 431 to 441. Note that to perform the broadening correction proscribed by Eq. (20), one does not need β, or $x_0$, so they will not be presented in the results table below, but they were included to insure that the nonlinear minimization worked correctly.

| Parameter | Value |
|---|---|
| σ' | 0.0636 sec |
| w' | 3.178 sec |
| τ'₀ | 21 sec |

These results can be interpreted by noting that σ<<w, implying that, as expected, the dominant broadening effect is mixing, not Gaussian diffusion or instrumental broadening. The $\tau_0$ parameter simply indicates that the sample took 21 seconds to traverse between the two instruments. In this context Eq. (20) can be rewritten as $$LS^b(t) = \int_{-\infty}^{\infty} LS(t-\tau)B(\sigma', w', \tau-\tau'_0)d\tau. \quad (22)$$

Figure 3:
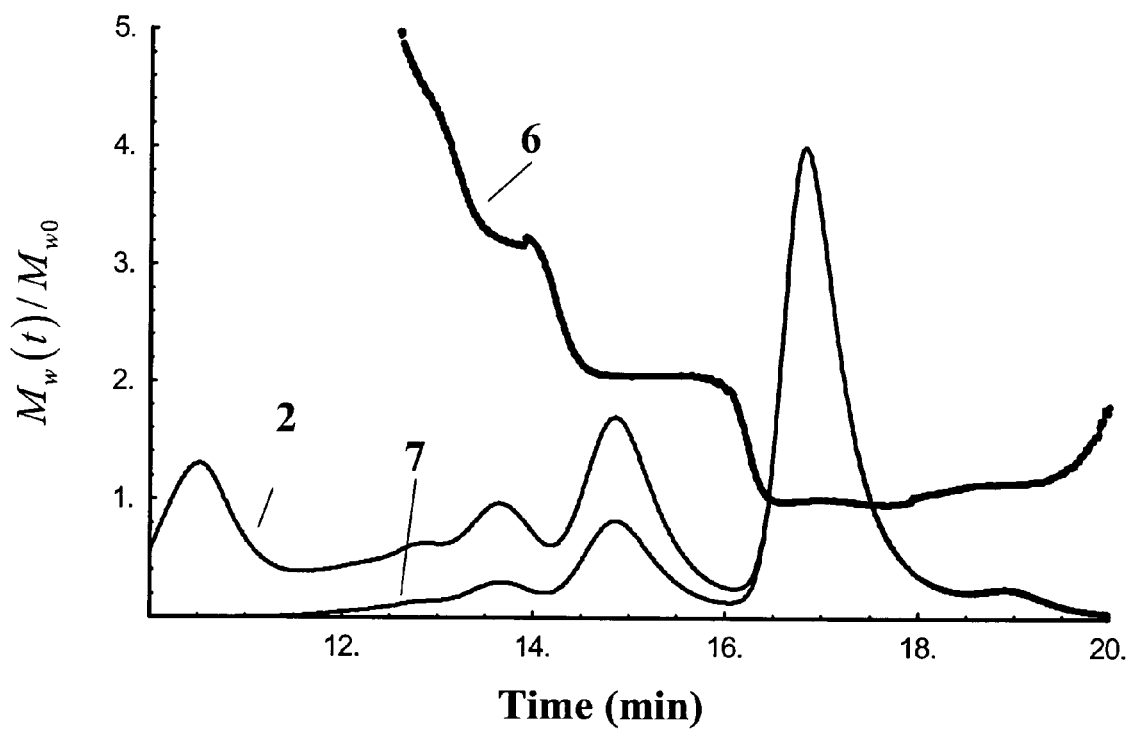
FIG. 3 shows the data of FIG. 1 corrected by the method of the invention.

FIG. 3 shows the broadened light scattering signal 7 computed using Eq. (22) with the fit parameters found in the first step above. The light scattering analysis proceeds as before using Trace 7 instead of the original light scattering data. The results are shown in Trace 6. There are a number of features to notice. First is that Trace 7 now overlaps Trace 2 at the monomer peak. This shows that model is correct, and that the nonlinear minimization worked properly. The second observation is that the dimer peak, between 14.5 mm and 16 mm, is now also a plateau as expected. The trimer peak, between 13.5 mm and 14.5 mm is also flatter, but since it was not baseline separated from its neighboring peaks, the results are less clear. The next observation is that the plateaus are now integral multiples of each other. This is to be expected since the molar mass of the dimer should be exactly twice the mass of the monomer. Similarly, the trimer plateau is now three times that of the monomer.

Figure 4:
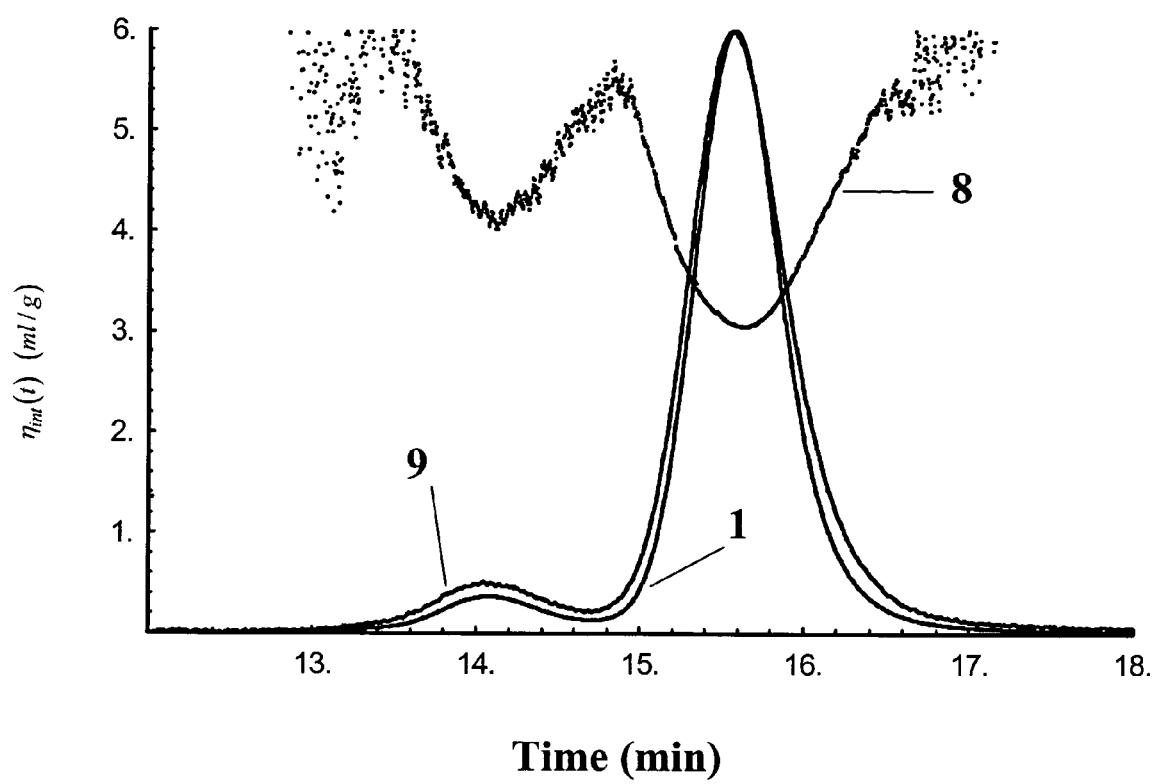
FIG. 4 shows an uncorrected plot of intrinsic viscosity versus elution volume for a BSA sample with a dRI detector downstream of viscometer.

FIG. 4 shows data from an 100 μl injection of BSA into a Shodex OH pack KW protein separation column. The flow rate was 0.5 ml/min. The fractionated sample first passed an online bridge viscometer and then through a dRI detector. The viscometer measures the specific viscosity which is defined as $$\eta_{sp}(t) = \eta(t)/\eta_0 - 1, \quad (23)$$

where η(t) is the viscosity of the fluid sample combination and $\eta_0$ is the viscosity of the pure fluid. The dRI detector measures the refractive index of the sample which can be converted to concentration if the sample dn/dc is known. One can then compute the intrinsic viscosity defined as $$\eta_{int}(t) = \lim_{c \to 0} \eta_{sp}(t)/c(t). \quad (24)$$

If the concentration is sufficiently low then the intrinsic viscosity can be approximated as $$\eta_{int}(t) \approx \eta_{sp}(t)/c(t). \quad (25)$$

Trace 9 is the specific viscosity, and trace 10 is the dRI signal. Traces 9 and 10 have been normalized to have the same maximum height. The vertical scale for these two traces is arbitrary. The results of this measurement are shown in Trace 8 which presents the intrinsic viscosity on the vertical axis in units of ml/g. The intrinsic viscosity should be constant across each sample peak. The curvature seen is due to interdetector broadening, but in this case the viscometer signal is substantially broader than the dRI signal. This is because the viscometer measures the viscosity over a much larger fluid volume than the dRI. In this example, the dominant broadening is instrumental broadening internal to the viscometer. In fact, the dRI signal is broadened by the passage of the sample between the two detectors, which reduces the overall difference in peak widths. The method of this invention can be applied as before, but in this case, the dRI signal will be broadened to match the viscosity signal. The first step in the algorithm is to choose a broadening model. Again the hybrid Gaussian-mixing model was used. The second step in the algorithm is to choose a monodisperse peak on which to determine the fit parameters. The monomer peak between 15.2 min and 16.2 min was used. As before Eq. (19) can be rewritten as $$\chi^2(\beta, \tau_0, \sigma, w, x_0) = \int_{peak}\left(\eta_{sp}(t) - \beta \int_{-\infty}^{\infty} dRI(t-\tau)B(\sigma, w, \tau-\tau_0)d\tau + x_0\right)^2 dt, \quad (26)$$

and the fit parameters are determined by minimizing $\chi^2$ with respect to the adjustable parameters. We find the fit parameters

| Parameter | Value |
|---|---|
| σ' | 0.01 sec |
| w' | 9.04 sec |
| τ'$_0$ | 15.6 sec |

Figure 5:
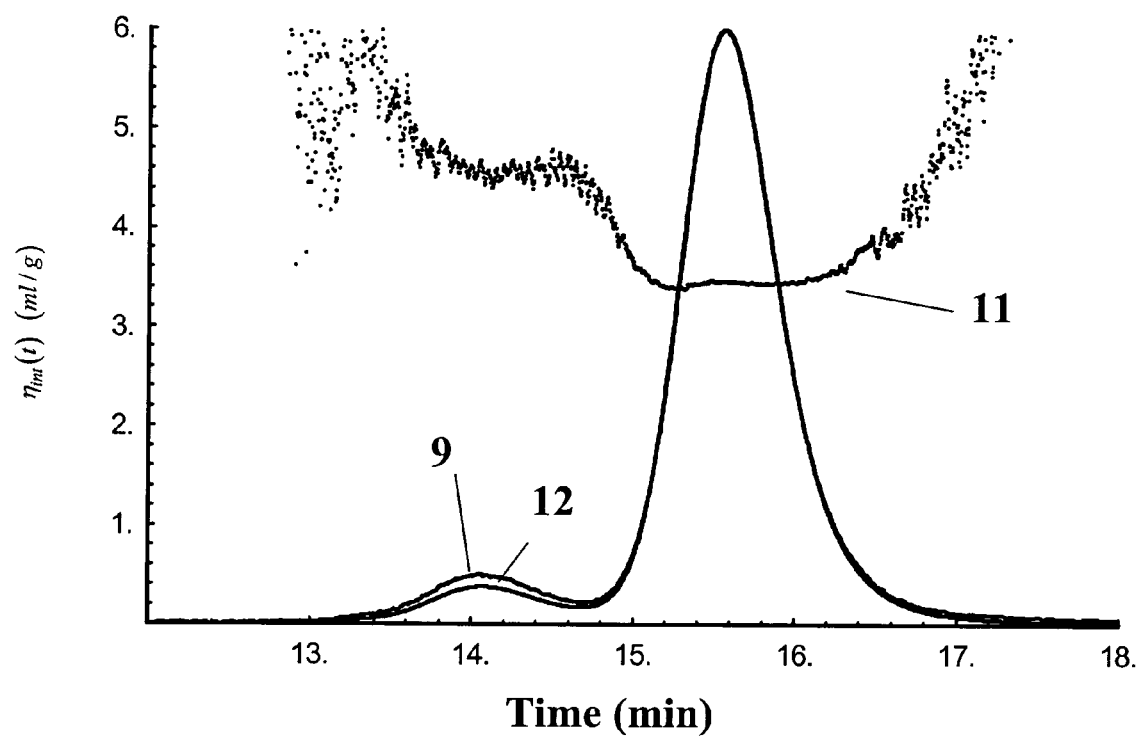
FIG. 5 shows the data of FIG. 4 corrected by the method of the invention. Trace 11 is the corrected intrinsic viscosity

In this case, the parameter w is 9.04 seconds, which arises not so much from inter-detector mixing, but from the large internal volume of the viscometer capillaries relative to the volume of the dRI flow cell. The Gaussian term is extremely small, which again indicates the diffusion is insignificant. The dRI signal may be broadened by rewriting Eq. (20) as $$dRI^b(t) = \int_{-\infty}^{\infty} dRI(t-\tau)B(\sigma', w', \tau-\tau'_0)d\tau, \quad (27)$$

and the analysis can proceed with the broadened dRI signal. FIG. 5 shows the broadened dRI signal in Trace 12 and the corrected intrinsic viscosity signal is shown in Trace 11. The results now consist of plateaus for each peak.

Figure 6:
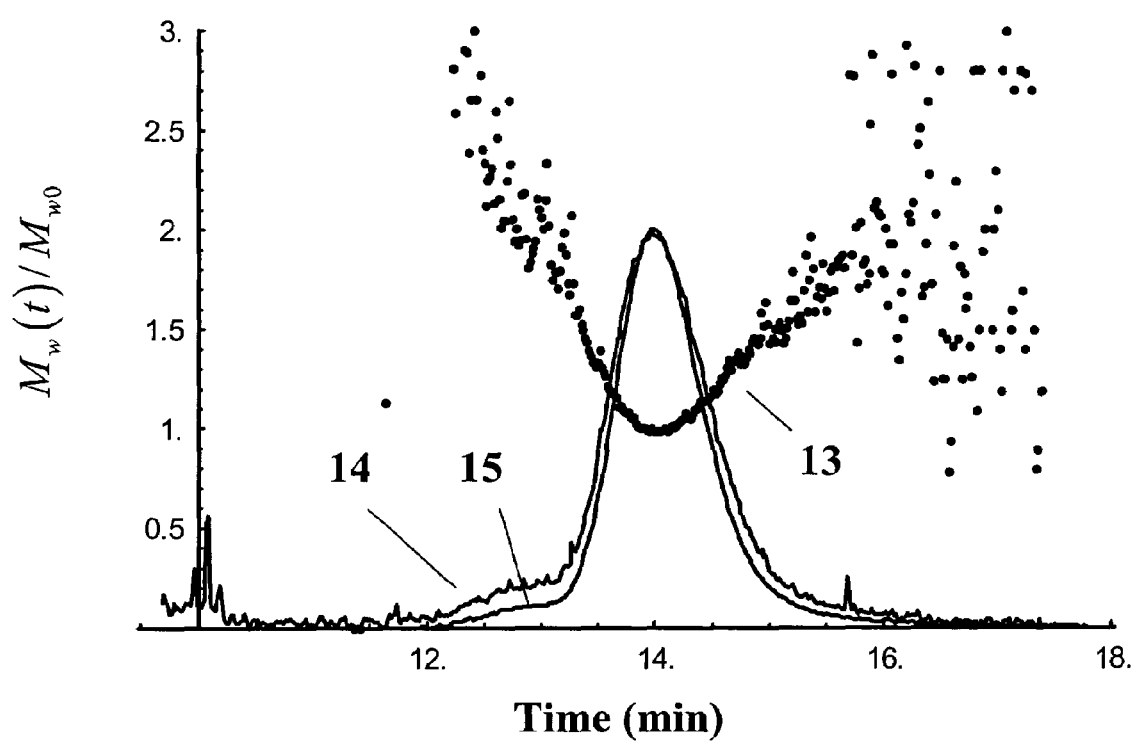
FIG. 6 shows an uncorrected plot of the molar mass of a BSA sample with a UV detector upstream of the MALS.

The last example, illustrated in FIG. 6, consists of a 100 µl sample of 3.0 mg/ml BSA measured by a UV detector followed by a MALS detector. In this case, the LS signal shown at 14 is significantly broader than the UV signal at 15, giving rise to the curved molar mass trace shown at 13. For this example, the UV signal will be broadened to match the LS signal. Equation (19) is rewritten as $$\chi^2(\beta, \tau_0, \sigma, w, x_0) = \int_{peak}\left(LS(t) - \beta \int_{-\infty}^{\infty} UV(t-\tau)B(\sigma, w, \tau-\tau_0)d\tau + x_0\right)^2 dt. \quad (28)$$

Again the hybrid mixing and Gaussian model is used, and the monomer peak between 13.5 min and 15 min is used to determine the fit parameters. Minimizing $\chi^2$ with respect to the fit parameters yields

| Parameter | Value |
|---|---|
| σ' | 0.22 sec |
| w' | 3.61 sec |
| τ'$_0$ | 39.5 sec |

Figure 7:
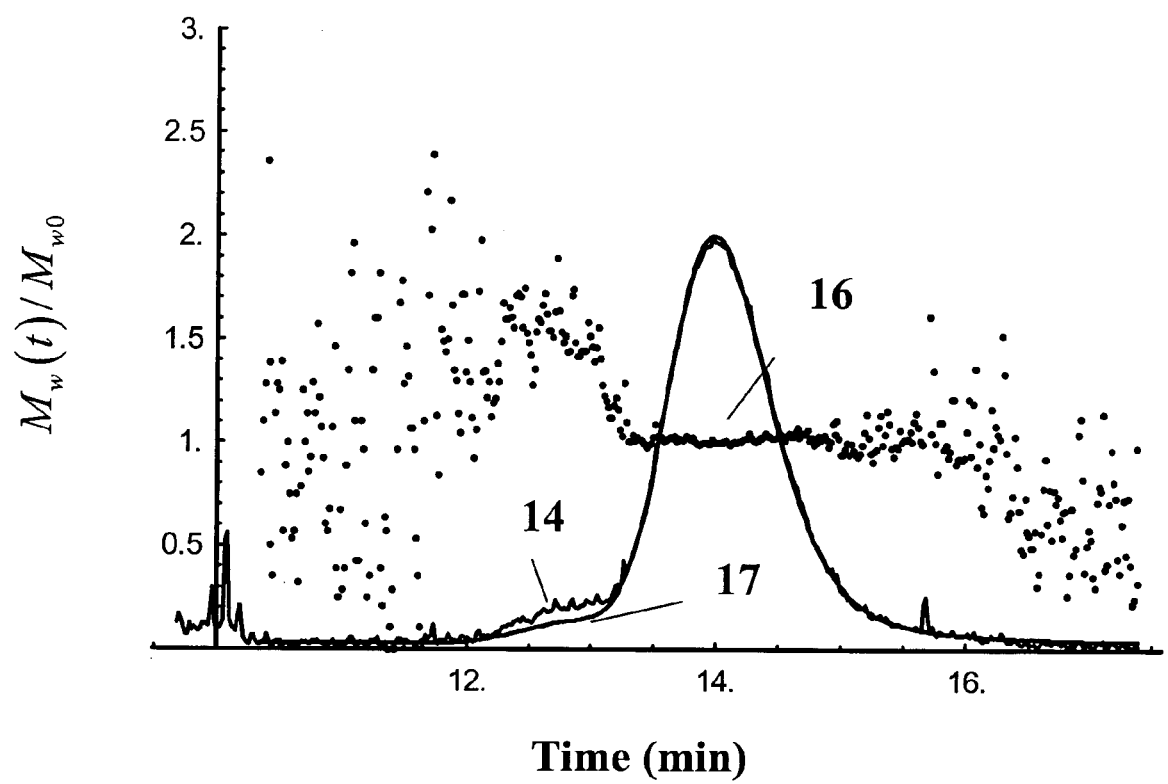
FIG. 7 shows the data of FIG. 6 corrected by the method of the invention.

Again, the dominant source of broadening is internal mixing. The UV data is now broadened, as shown in FIG. 7 by computing Eq. (20) rewritten as $$UV^b(t) = \int_{-\infty}^{\infty} UV(t-\tau)B(\sigma', w', \tau-\tau'_0)d\tau. \quad (29)$$

The broadened UV signal is shown in Trace 17, and the molar mass is shown in Trace 16. As with the previous two cases, the data consists of plateaus, and the effects of inter-detector broadening are dramatically reduced.

Figure 8A:
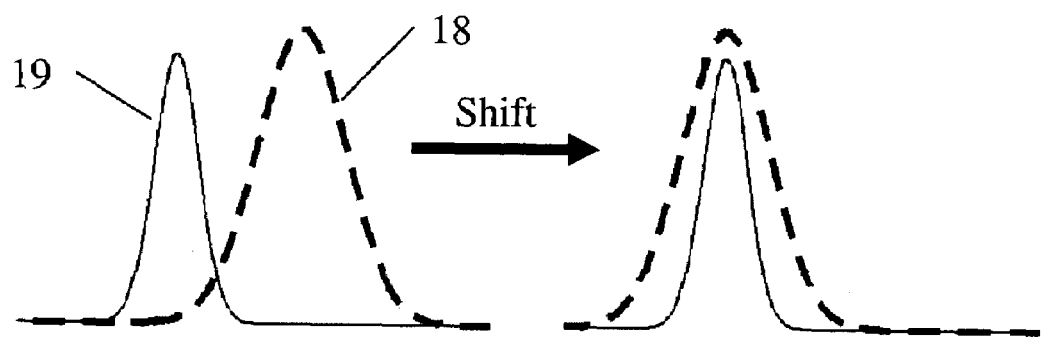
FIG. 8 is a graphical representation of the algorithm.
Figure 8B:
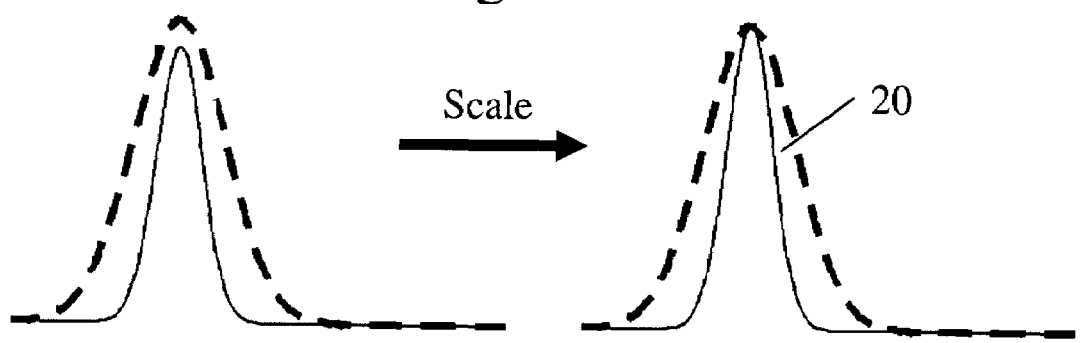
Figure 8C:
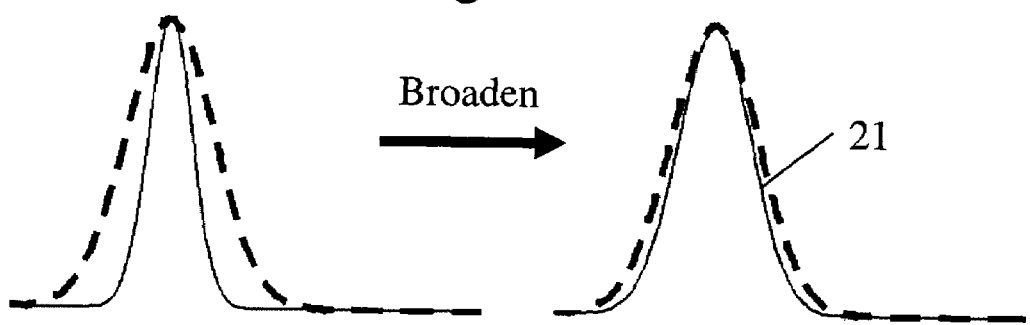
Figure 8D:

The foregoing demonstration of the inventive method illustrates but a few of the possible types of band broadening corrections that may be addressed and corrected by the inventive methods disclosed in this specification. As will be obvious to those skilled in the chromatographic arts, until this invention, the effects of band broadening have represented significant impediments to improving the precision of measurements associated with the use of multiple detectors. This inventive method and all its variants fulfill the expectation that band broadening effects will thereby be reduced dramatically. Accordingly, I claim The invention is clearly described above in a manner that is understandable to one skilled in the mathematical data analysis arts; however, in order to make the invention more readily understandable, FIG. 8 is presented which graphically illustrates the method of correcting for band broadening using Eq. (19). FIG. 8a shows detector signals, $D_1$ (t), 18, and $D_2$ (t), 19. The function presented in Eq. (19) can be decomposed into the following steps. First the detector signal with the narrowest peak, 19, is identified as the signal that will be corrected, i. e. will be broadened. Signal 19 is then shifted by the interdetector time, $\tau_2$ so it comes into alignment with signal 18. As shown in FIG. 8b, it is scaled by $\beta_2$ so that it is on the same scale/height as the broadest peak, 18. This newly processed signal peak 20 is then broadened with the model $B(\alpha_{2j}, \tau-\tau_2)$. As shown in FIG. 8c, the broadened data 21 is finally compared to the data of the unprocessed broad peak 18 by computing a $\chi^2$ model which is then minimized to determine optimal values of $\beta_2, \alpha_{2j}, \tau_2$. FIG. 8d compares the data after the $\chi^2$ minimization has been completed, i. e., the peaks from the two detectors overlay. It should be stressed that Eq. (19) accomplishes all of these steps simultaneously, as would be obvious to those trained in the art. Although FIG. 8 has been shown in sections for pedagogical reasons, the execution of the least squares process of Eq. (19) is done in a single calculation.

What is claimed is:

1. A method to determine the best fit parameters of a broadening model to be used to correct for the effects of interdetector band broadening in a chromatographic separation containing a separation device followed by two or more detectors i (=1,n), where n is the number of detectors, comprising the steps of
    A. Selecting a broadening model $B(\alpha_0, \alpha_1, \ldots, \alpha_l, t)$ containing a set of adjustable parameters $\alpha_j$(=0, ..., l), where l is the number of adjustable parameters;
    B. Injecting a reference sample of uniform composition;
    C. Collecting the i detector signals $D_i(t)$ as a function of time corresponding to a peak of said sample from each of said detectors of where a peak is defined as a range of time during which the sample of uniform composition elutes;
    D. Defining the reference signal $D_n(t)$ as that which exhibits the broadest temporal response;

E. For each detector i, forming a $\chi_i^2$ model which is derived from said broadening model, and is to be minimized over said peak using said signal $D_n(t)$ as a reference against which the said detector i is to be compared;

$$\chi_i^2(\beta_i, \tau_i, \alpha_{ij}) = \int_{peak} \left( D_n(t) - \beta_i \int_{-\infty}^{\infty} D_i(t-\tau) B(\alpha_{ij}, \tau-\tau_i) d\tau \right)^2 dt,$$

where said best fit parameters are $\beta_i$, $\alpha_{ij}$, and $\tau_i$; and
  (a) $\beta_i$ is the scale factor for detector i;
  (b) $\alpha_{ij}$ characterizes the extent of the broadening for detector i and parameter j; and
  (c) $\tau_i$ is the interdetector time delay for detector i.
F. Minimizing said $\chi_i^2$ models to determine yield said best fit parameters for said detector peak.

2. The method of claim 1 where the minimization of said $\chi_i^2$ models are achieved by use of a nonlinear least squares algorithm.

3. The method of claim 2 where said nonlinear least squares algorithm is of the type developed by Marquardt.

4. The method of claim 1 where said interdetector band broadening is caused by dilution.

5. The method of claim 1 where said interdetector band broadening is caused by mixing.

6. The method of claim 1 where said interdetector band broadening is caused by mechanical defects within the detector cells andlor connectors thereto.

7. The method of claim 1 where said interdetector band broadening is caused by internal instrumental averaging.

8. The method of claim 7 where said internal instrumental averaging is from electronic filtering.

9. The method of claim 7 where said internal instrumental averaging is by measuring a range of volumes of the sample.

10. The method of claim 1 where said peaks of uniform composition correspond to monodisperse fractions which are separated from the other fractions by said chromatographic separation.

11. The method of claim 1 where said peaks of uniform composition correspond respectively to fractions for which said separation device is ineffective and produces no appreciable separation so that said sample elutes with a uniform composition.

12. The method of claim 1 where said broadening model is given by $$B(\alpha_1, \alpha_2, t) = \int_{-\infty}^{\infty} \frac{1}{\alpha_1 \sqrt{2\pi}} e^{-\tau^2/2\alpha_1^2} \frac{1}{\alpha_2} U(t-\tau) e^{-(t-\tau)/\alpha_2} d\tau,$$

where $\alpha_1$ and $\alpha_2$ are parameters that characterize said interdetector band broadening; the parameter $\alpha_1$ characterizes Gaussian broadening due to internal instrumental averaging, and $\alpha_2$ characterizes an interdetector mixing volume; and where $U(t-\tau)=1$ when $t \geq \tau$ and $U(t-\tau)=0$ when $t<\tau$.

* * * * *